United States Patent [19]

Osuga et al.

[11] Patent Number: 4,534,330

[45] Date of Patent: Aug. 13, 1985

[54] AIR/FUEL RATIO DETECTOR

[75] Inventors: Minoru Osuga; Yoshishige Oyama, both of Katsuta, Japan

[73] Assignee: Hitachi, Ltd., Tokyo, Japan

[21] Appl. No.: 575,666

[22] Filed: Jan. 31, 1984

[30] Foreign Application Priority Data

Feb. 4, 1983 [JP] Japan .................................. 58-16037

[51] Int. Cl.³ ........................ F02B 3/00; F02B 75/10; F02M 7/00; F02M 23/04
[52] U.S. Cl. .................................... 123/440; 123/481; 204/421
[58] Field of Search ............... 123/440, 489, 434, 445; 204/195.5

[56] References Cited

U.S. PATENT DOCUMENTS

| | | | |
|---|---|---|---|
| 4,132,200 | 1/1979 | Asano et al. | 123/440 |
| 4,183,335 | 1/1980 | Asano et al. | 123/440 |
| 4,208,993 | 6/1980 | Peter | 123/440 |
| 4,210,106 | 7/1980 | Wessel et al. | 123/489 |
| 4,228,775 | 10/1980 | Schweikert | 123/489 |
| 4,237,839 | 12/1980 | Ueno et al. | 123/440 |
| 4,300,505 | 11/1981 | Takada et al. | 123/489 |
| 4,337,745 | 7/1982 | Pomerantz | 123/440 |
| 4,338,900 | 7/1982 | Dilger et al. | 123/440 |
| 4,378,773 | 4/1983 | Ohgami | 123/489 |
| 4,392,471 | 7/1983 | Miyogi et al. | 123/440 |

Primary Examiner—Raymond A. Nelli
Attorney, Agent, or Firm—Antonelli, Terry & Wands

[57] ABSTRACT

A sensor for detecting an air/fuel ratio is fitted to an exhaust pipe of an internal combustion engine so as to effect feedback control and to keep the air/fuel ratio of the engine at a predetermined value. To improve the feedback control accuracy, the sensor response must be increased. If the response is increased too much, however, the sensor output is found deviated from the true air/fuel ratio, and the deviation quantity is also found proportional to the change of the air-fuel ratio with respect to time. The invention makes it possible to make appropriate air/fuel ratio control by compensating for the output signal of the sensor using the signal component based upon the change of the air/fuel ratio with time, among the sensor output signals.

6 Claims, 47 Drawing Figures

SENSOR A

SENSOR B

FIG. 6(a)
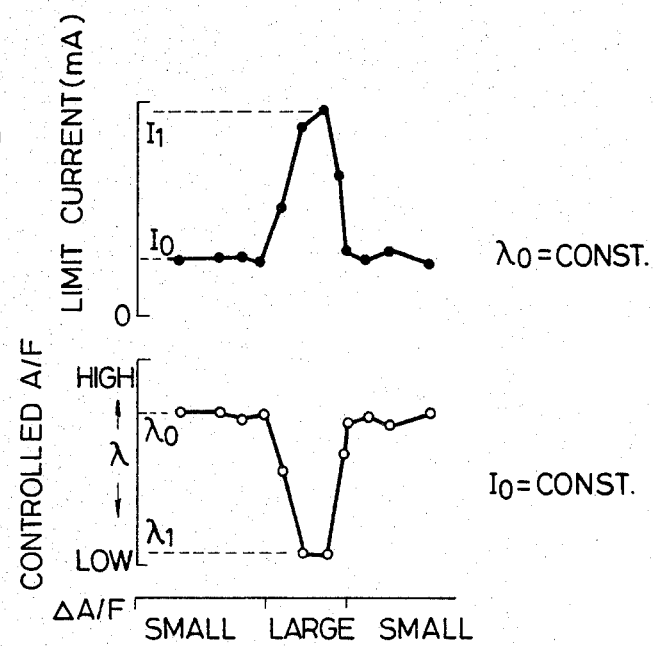
FIG. 6(b)
FIG. 7
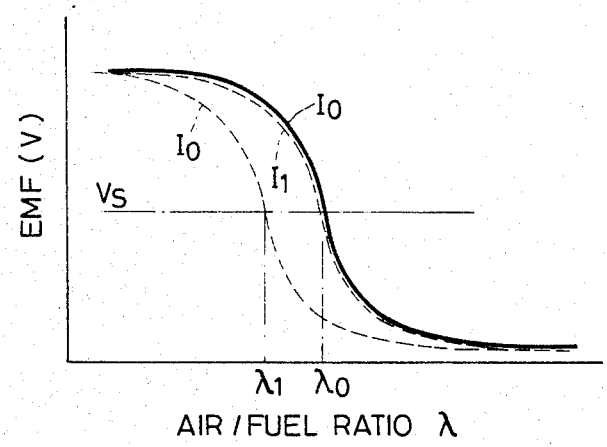

TIME t

→ TIME t

AVERAGE A/F=CONST.

AIR/FUEL RATIO DETECTOR

BACKGROUND OF THE INVENTION

This invention relates to an air/fuel ratio detector. More particularly, the present invention relates to an air/fuel ratio detector suitable for use in air/fuel ratio control.

Prior art air/fuel ratio detectors include those which detect the ratio on the leaner side of the stoichiometric air/fuel ratio and those which detect the ratio on the richer side of the stoichiometric air/fuel ratio, as disclosed for example in U.S. Pat. Nos. 4,304,652 and 4,300,990. When these detectors are used for the air/fuel ratio control of an internal combustion engine, for example, the detectors must have quick response in order to effect feedback control.

Accordingly, the inventors of this invention produced a wide variety of air/fuel ratio sensors and examined their response characteristics. As a result of studies, the inventors found that if the response speed of the sensors is increased, the sensor output fails to represent a true value and accurate air/fuel ratio control becomes impossible to produce.

SUMMARY OF THE INVENTION

On the basis of the finding described above, the present invention is directed to provide an air/fuel ratio detector which has quick response and can be used for accurate air/fuel ratio control.

The inventors examined the sensors having quick response and found that the deviation of the sensor output from the true value became great particularly when the change of the air/fuel ratio with respect to time was great. The present invention contemplates therefore to compensate for the sensor output on the basis of the change signal component in the sensor output resulting from the change of the air/fuel ratio with respect to time.

First, the relation between the change of the air/fuel ratio with respect to time and the sensor output will be principally explained on the results of experiments carried out by the present inventors.

FIGS. 1(a)–1(d) illustrate the basic construction of an example of the air/fuel ratio sensor and its characteristics. FIG. 1(a) illustrates the principle of the sensor, and electrodes 21a, 21b are shown disposed on both sides of a solid electrolyte 3. A porous diffusion resistor 22 is disposed on the surface of the electrode 21a. When a potential is applied from a power source 23 across an anode 21b and a cathode 21a, oxygen $O_2$ moves in the direction represented by an arrow in the drawing.

Here, the power source 23 is a constant current source. If a current I is caused to flow and the electromotive force (EMF) at that time is measured, the relation between the air/fuel ratio and EMF changes stepwise as shown in FIG. 1(b). The points where the air/fuel ratio changes varies depending upon the current applied, and the greater the current value, the closer to the lean side becomes the change point of the air/fuel ratio. Air/fuel ratio control of an engine is effected by utilizing the points which thus change step-wise. When the current value is zero, it changes at the stoichiometric air/fuel ratio point.

FIG. 1(c) shows the characteristics of the sensor when the power source 23 is used as a constant voltage source. When the voltage V applied to the sensor is changed as shown in FIG. 1(d), a limit current $I_o$ proportional to the oxygen concentration can be obtained. In other words, an analog output proportional to the oxygen concentration can be obtained if the voltage applied to the sensor is kept at $V_o$ at which the limit current $I_o$ is obtained. FIG. 1(c) shows such characteristics and a current value proportional to the air/fuel ratio can be obtained. Air/fuel ratio control of the engine is effected by detecting this current value, too.

FIG. 2 shows sensors A and B to explain the problem with the air/fuel ratio sensors. The sensor A shown in FIG. 2(a) has a thin diffusion resistor 22a and quick response but the sensor output fluctuates in accordance with the variation of the air/fuel ratios. On the other hand, the sensor B shown in FIG. 2(b) has a thick diffusion resistor 22b, which is greater than that of the sensor A, and slow response. Hence, it can not follow up the variation of the air/fuel ratios and the fluctuation of the sensor output is small. That is to say, inside the range in which the air/fuel ratio fluctuates, the output of the sensor A also fluctuates so that the limit current value described above deviates from the line of FIG. 1(c) proportional to the oxygen concentration, and hence, a true value is no longer represented. The sensor B having slow response does not cause such a problem. This will be illustrated by experimental data.

FIG. 3 is a diagram of the characteristics of FIG. 1(d) and shows the result of measurement of the current flowing through the sensors A and B that are fitted to an exhaust pipe, respectively, when the voltage applied to the sensors is changed. During the measurement, the mean air/fuel ratio (A/F) was kept constant by keeping constant the intake air quantity and fuel supply quantity to the engine. The engine was operated inside a range where A/F changed remarkably. As shown in FIG. 3, the signal of the sensor A having quick response fluctuated greatly but the signal of the sensor B having slow response exhibited small fluctuation as represented by a curve B. The difference between the limit current values $I_a$ and $I_b$ resulted from the deviation of the signal of the sensor A from the true value and from the difference between the diffusion resistors 22a and 22b.

The reason why the signal of the sensor A deviates from the true value may be as follows. The oxygen concentration inside the exhaust pipe changes in synchronism with the revolution of the engine. When the oxygen concentration changes from the high side to the low, the limit current drops in accordance with this change, but since the response of the sensor A is too good, the oxygen in the proximity of the electrode, which is covered with the thin diffusion resistor 22a, becomes temporarily short, so that the state changes from the ion conduction to the electron conduction. Hence, the current to be measured becomes greater.

FIG. 4 illustrates comparatively the limit current values $I_a$ and $I_b$ of the sensors A and B when the number of revolutions of the engine is increased to enlarge the variation of the air/fuel ratio A/F while the mean air/fuel ratio is kept constant. $I_a$ of the sensor A increases with the increase of $\Delta A/F$ but $I_b$ of the sensor B hardly changes. In other words, $I_a$ is not proportional to the air/fuel ratio when the sensor output fluctuates greatly in response to $\Delta A/F$ as in the case of the sensor A.

FIG. 5 illustrates the result of measurement of the change of the limit current of the sensors A and B with respect to the excess air ratio. This drawing corresponds to FIG. 1(c). Line A-1 represents the characteristics measured in a range where no disturbance of the air/fuel ratio $\Delta A/F$ exists, by the sensor A. Line A-2 represents the result of measurement in a range where $\Delta A/F$ is great. As can be seen from the diagram, the line A-2 corresponding to large $\Delta A/F$ deviates greatly from the line A-1 annd loses its linearity. Similarly, lines B-1 and B-2 represent the output of the sensor B in a range where $\Delta A/F$ is small and in a range where $\Delta A/F$ is great, respectively. However, both lines are in agreement and linearity of the output of the line B-2 is not lost.

When measuring the air/fuel ratio of the engine by detecting this limit current value, the increase of the sensor response results in the problem that the output does not represent the true value when $\Delta A/F$ ($\lambda_o$) is great and if the response is reduced, on the other hand, the output represents the true value but the slow response itself is another problem.

Next, the problem encountered when air/fuel ratio control is effected by means of the change of EMF using the sensor A will be described.

FIG. 6(a) shows the result of measurement of the limit current in a range where $\Delta A/F$ is great and in a range where it is small, while mean A/F is kept constant. When $\Delta A/F$ is small, the limit current is Io but where $\Delta A/F$ is great, the limit current becomes great such as $I_1$. FIGS. 6(a) and 6(b) illustrate the results of measurement in an open loop and a closed loop, respectively. FIG. 6(b) shows the result of the controlled A/F when the limit current $I_o$ to be applied to the sensor A is kept constant and closed loop control is effected so as to keep the air/fuel ratio constant by change of the electromotive force. When $\Delta A/F$ is small, A/F is controlled to $\lambda_o$ but where $\Delta A/F$ is great, A/F is controlled to $\lambda_1$ on the richer side.

FIG. 7 illustrates the change of the electromotive force of the sensor A under the conditions of FIG. 6. When the mean air/fuel ratio ($\lambda_o$) is kept constant as shown in FIG. 6(a), the limit current changes from $I_o$ to $I_1$ by $\Delta A/F$. Nonetheless, if control is made with the limit current $I_o$ being kept constant as shown in FIG. 6(b), it corresponds to the case where control is made by $I_o$ represented by dash line in FIG. 7 when $I_o$ represented by solid line is caused to flow through the sensor A, although the change point of the electromotive force changes from $\lambda_o$ to $\lambda_1$. Hence, the controlled air/fuel ratio changes to $\lambda_1$. To keep the controlled air/fuel ratio constant at $\lambda_o$, it is necessary to cause the limit current $I_1$, that is changed afresh from I, to flow through the sensor A. Incidentally, symbol $V_s$ represents a slice level used for control.

The limit current value and the controlled air/fuel ratio when $\Delta A/F$ of the sensor B is changed exhibit substantially the constant values irrespective of $\Delta A/F$. However, since its response is slow, the sensor is not suitable for control use but can be suitably used for the calibration of the air/fuel ratio.

As described in detail above, the output of the sensor A having quick response does not represent the true value whether the control is made by the current or by the voltage in a range where $\Delta A/F$ is great.

The gist of the present invention resides in that compensation processing is made for the sensor output on the basis of the change signal components in the sensor output resulting from the change of the air/fuel ratio with respect to time, as described earlier.

BRIEF DESCRIPTION OF THE DRAWINGS

FIGS. 13a, 13b through 15a–15c schematically illustrate still another embodiment of the present invention;

DESCRIPTION OF THE PREFERRED EMBODIMENTS

Hereinafter, one embodiment of the present invention will be described with reference to the drawings.

First, the air/fuel ratio sensor of the first embodiment will be explained with reference to FIG. 8.

Figure 8A:
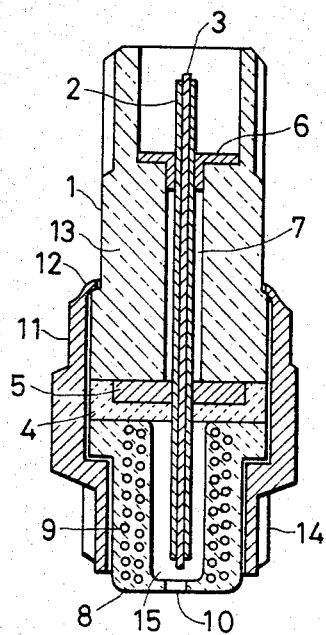
FIGS. 8a, 8b, 9a, 9b and 10 schematically illustrate one embodiment of the present invention.

FIG. 8(a) shows the construction of the air/fuel ratio sensor 1 of this embodiment. A sensor portion 2 consists of a solid electrolyte 3 and electrodes printed on both sides of the electrolyte. The sensor portion 2 is fixed to a holder 13 by a non-conductive washer 4, a rod-like fixing member 5 and a stopper 6 having a hole. An atmospheric chamber 7 communicates with the atmosphere through the hole of the stopper 6. A heater 9 is embedded into a cover 8 and an exhaust hole 10 for the passage of an exhaust gas is bored on the cover 8. An adaptor 11 is integrated with the holder 13 by a caulking portion 12. The adaptor 11 is fitted to an exhaust pipe 15 at its screw portion 14. In other words, the exhaust gas enters the exhaust chamber 15 through the exhaust hole 10 and the atmosphere is introduced into the atmospheric chamber 7 through the hole of the stopper 6.

Figure 8B:
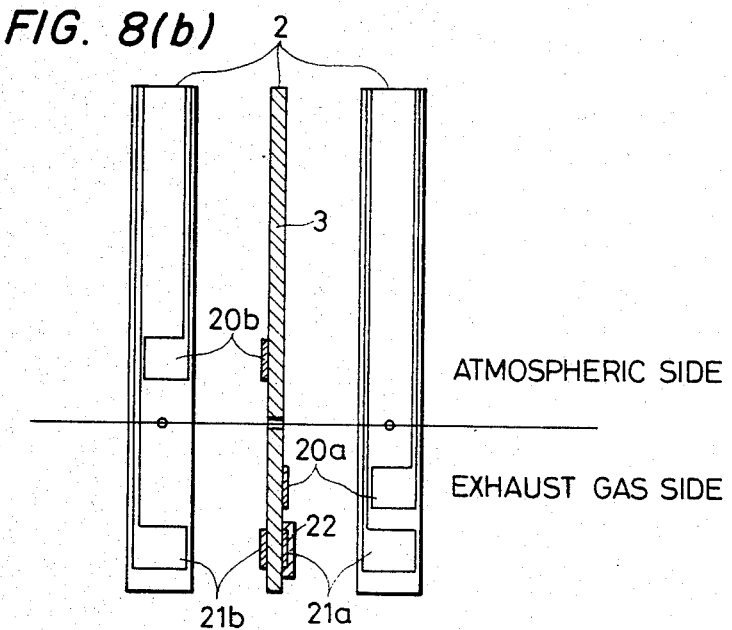

FIG. 8(b) illustrates in detail the sensor portion 2. The portion above dot-and-dash line is on the side of the atmospheric chamber 7 while the portion below the line is on the side of the exhaust chamber 15. The electrodes 20a, 20b are disposed on both sides of the solid electrolyte 3 to detect the point of the stoichiometric air/fuel ratio ($\lambda = 1.0$). The electrode 20a is the cathode and the electrode 20b is the anode. In other words, the point of the stoichiometric air/fuel ratio is the point at which the electromotive force rises when the potential of the anode 20b is being measured. Cathode 21a and anode 21b are printed below the electrodes 20a, 20b, respectively, to detect a lean air/fuel ratio. The cathode 21a is covered with a diffusion resistor 22. When a potential is applied to the anode 21b, the oxygen ion moves from the cathode 21a to the anode 21b. The limit current due to ion conduction flows by the movement of the oxygen ion in cooperation with the action of the diffusion resistor 22.

Figure 9A:
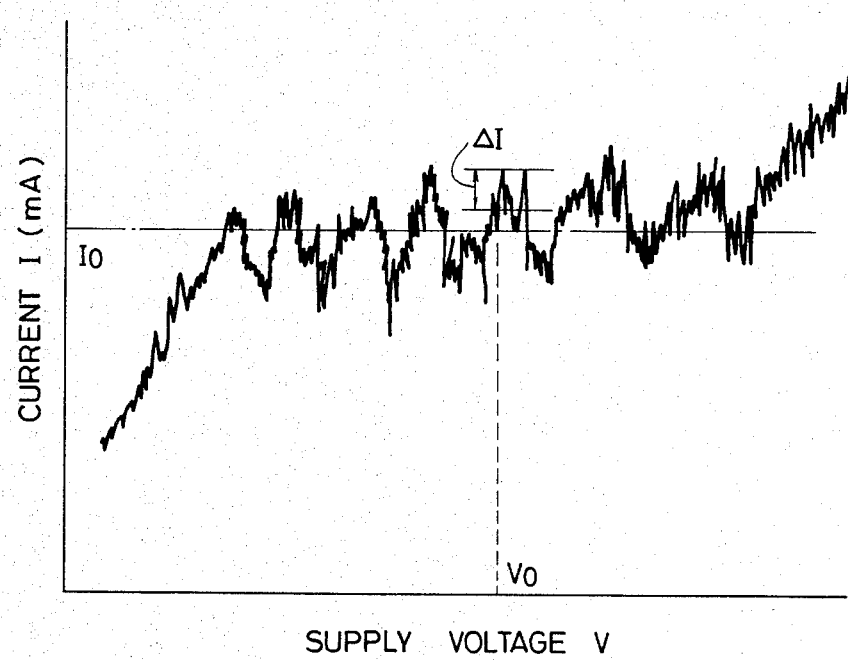

FIG. 9 shows the waveform of the limit current value when measured using the air/fuel sensor described above. The waveform in FIG. 9(a) represents the case where the fluctuation of the air/fuel ratio $\Delta A/F$ is great and the low and high frequency components overlap with each other. The degree of change of this high frequency component $\Delta I$ corresponds substantially to ΔA/F. In other words, when ΔA/F is great, ΔI becomes also great. The degree of fluctuation of ΔA/F can be determined by measuring this ΔI and the true value can be obtained by compensating the ΔI. The true limit current value $I_o$, can be given by the following equation, where $I_o$ represents the limit current value resulting from the low frequency component and ΔI represents the change current value resulting from the high frequency component:

$$I_o' = I_o - K \cdot \Delta I \tag{1}$$

Figure 9B:
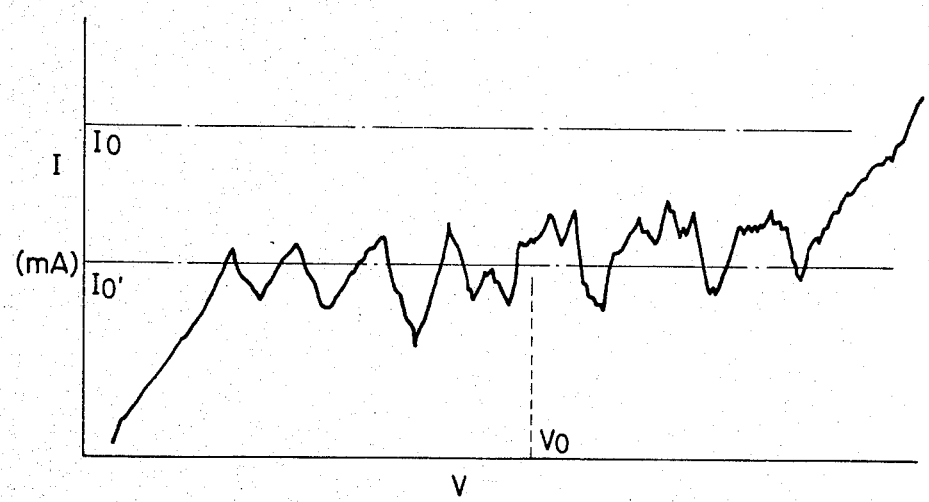

Here, K represents a compensation coefficient. When the waveform of FIG. 9(a) is converted on the basis of this formula, it becomes such as shown in FIG. 9(b). However, no change occurs in response.

Figure 10:
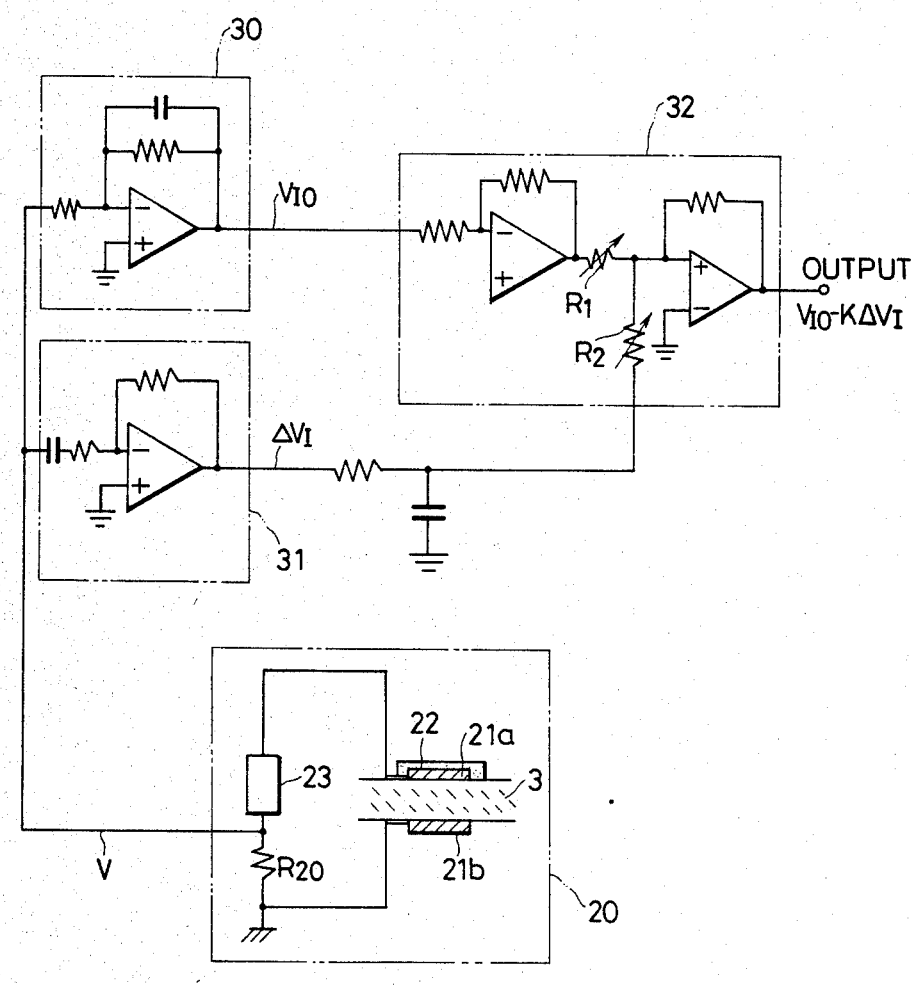

An example of the circuit construction to realize the equation (1) above will be explained with reference to FIG. 10. A predetermined voltage $V_o$ is applied between the electrodes 21a and 21b inside the sensor portion 20 from the power source 23. A limit current $I_o$ proportional to the air/fuel ratio flows through the resistor $R_{20}$. This current is detected as a terminal voltage V across the resistor $R_{20}$. The voltage V is applied to a low frequency detection circuit 30 and to a high frequency detection circuit 31. The low frequency detection circuit 30 is a lowpass filter which generates a low frequency voltage $V_{Io}$ of the voltage V. The high frequency detection circuit 31 is a highpass filter which generates a change voltage $\Delta V_1$ of the voltage resulting from the high frequency component V. This voltage $\Delta V_1$ is held. In an operation circuit 32, the voltage $V_{Io}$ is inverted and amplified and the sum of this voltage and the voltage $\Delta V_I$ that has been held is further amplified. Accordingly, the output becomes $V_{Io} - K \cdot \Delta V_I$. The compensation coefficient K can be selected suitably by selecting suitable values for the two input resistors $R_1$ and $R_2$ inside the circuit 32.

Figure 1A:
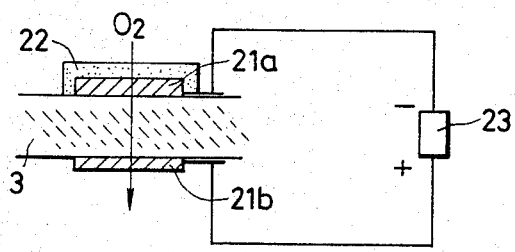
FIGS. 1a–1d, 2a, b, 6a&b and 7 illustrate the principle of the present invention.
Figure 1B:
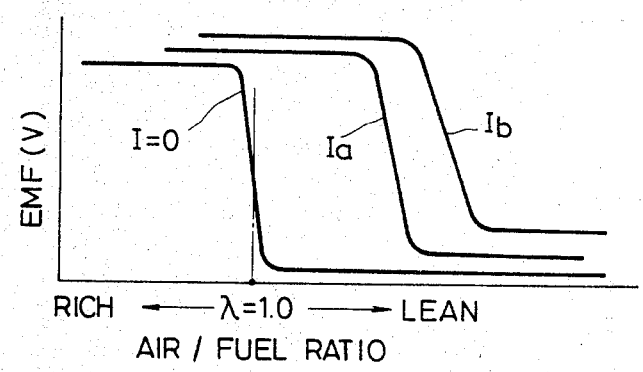
Figure 1C:
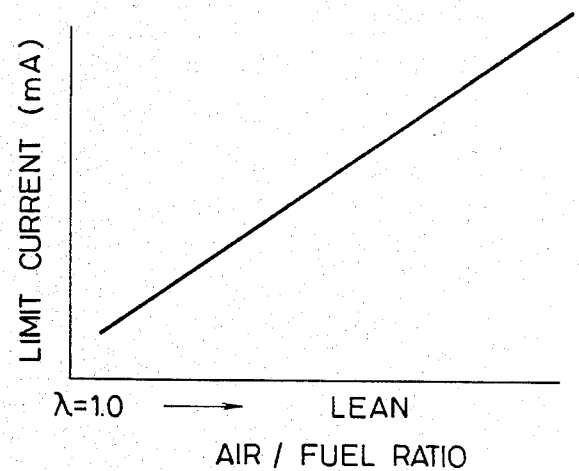
Figure 1D:
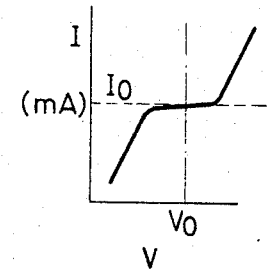
Figure 11A:
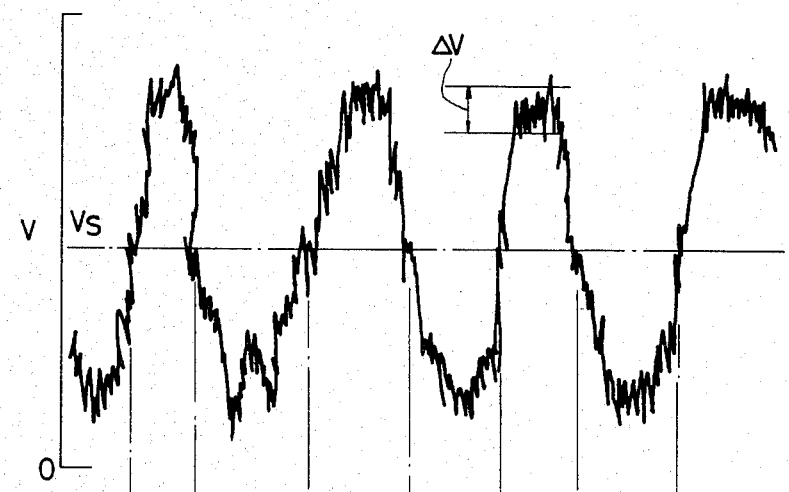
FIGS. 11a, 11b, and 12a–c schematically illustrate another embodiment of the present invention.
Figure 11B:
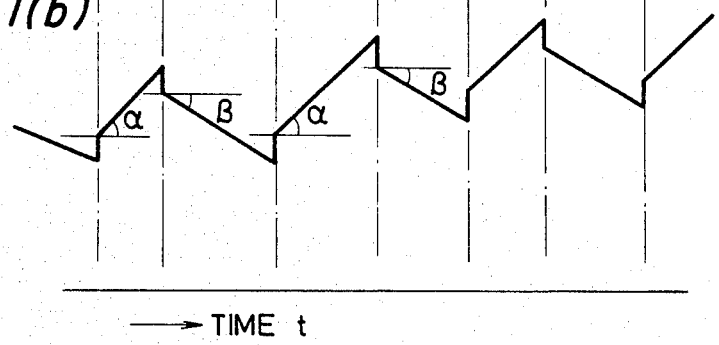

FIG. 11 illustrates another embodiment of the present invention which represents a compensation method when the air/fuel ratio is controlled by the change of the electromotive force by constant current excitation as shown in FIG. 1(b). FIG. 11(a) shows in detail the measured waveforms of the change of the electromotive force. Symbol $V_s$ represents the slice level. In this case, too, the waveform of the frequency component having high amplitude in proportional to ΔA/F is superimposed on the waveform of the low frequency component. The degree of ΔA/F is determined by detecting this ΔV by the highpass filter or the like. In other words, as shown in FIG. 6, when control is effected with a constant set current, the air/fuel ratio to be controlled becomes great if A/F, that is, ΔV, is great. Accordingly, the air/fuel ratio is kept in the predetermined lean state by changing the constant of the proportional integration control when the fuel quantity is subjected to the closed loop control. If the positive integration constant α and the negative integration constant β being different valves are changed so as to make the constant α larger than the constant β as shown in FIG. 11(b), the air/fuel ratio shifts to the lean side. Thus, the air/fuel ratio to be controlled is controlled to a desired value.

This control can be made digitally by utilizing a microcomputer. The control will be explained with reference to FIG. 12.

Figure 12A:
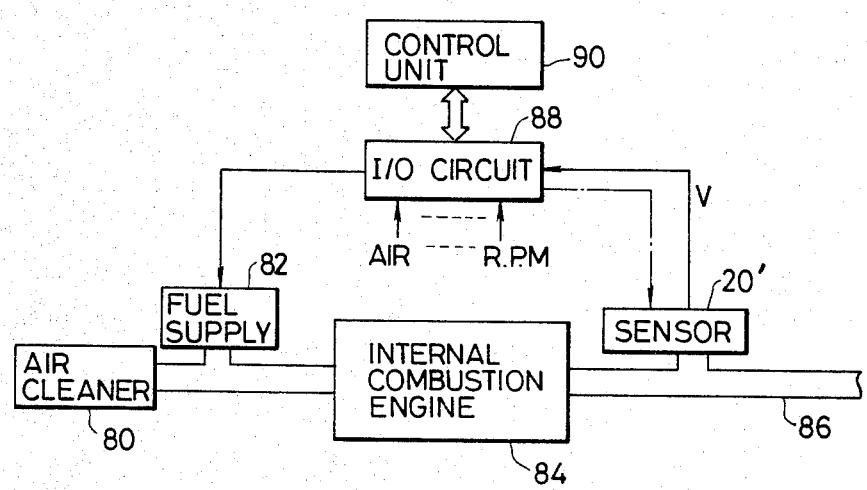
Figure 12B:
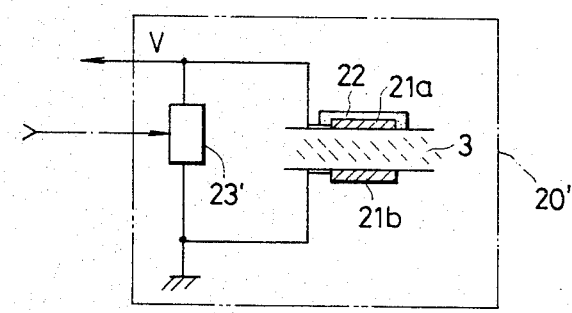
Figure 12C:
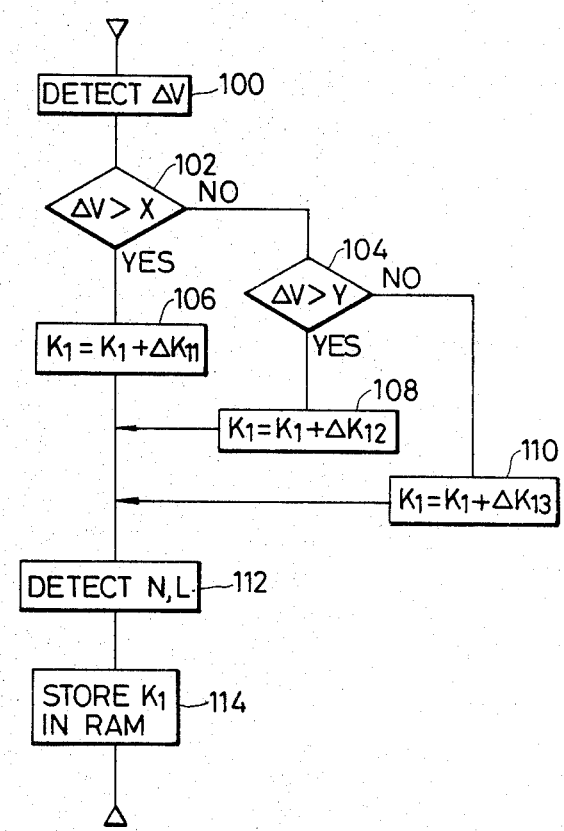

FIG. 12(a) is a block diagram of the internal combustion engine as a whole to be controlled, FIG. 12(b) is a detailed view of the sensor portion 20' and FIG. 12(c) is a flow chart.

The fuel is supplied from fuel supply means 82 such as an injector or an electronic control carburetor to the air which is sucked from an air cleaner 80. The air/fuel mixture is burnt in the internal combustion engine 84 and is discharged from an exhaust pipe 86. The sensor portion 20' is fitted to the exhaust pipe 86. The construction of this sensor portion 20' is substantially the same as that of the sensor 20 shown in FIG. 10 but the difference resides in that a current is used as the power source 23' and the electromotive force V generated between the electrodes 21a and 21b is measured. The electromotive force generated by the sensor 20' is coupled to a control unit 90 through an I/O circuit 88. This control unit 90 consists of a known CPU (central processing unit), ROM (read only memory) and RAM (random access memory). The control unit 90 receives the signal of an intake air quantity and the signal of the number of revolution through the I/O circuit 88 and delivers a control signal to the fuel supply means 82. Here, the sensor portion 20' and the control unit 90 constitute the air/fuel ratio detector of the present invention.

In FIG. 12(c), change value ΔV is read at a step 100. Judgement is then made at a step 102 whether or not ΔV is greater than a predetermined value X and judgement is made at a step 104 whether or not ΔV is greater than another predetermined value Y. In the case of an injector, the fuel jet time T for controlling the fuel quantity is given by the following equation:

$$T = t \times K1$$

where t is a fundamental injection time and K1 is a compensation coefficient.

The integration constants α and β are contained in the compensation coefficient K1. This compensation coefficient is further compensated for in accordance with the change value ΔV. That is, when ΔV is greater than X, the coefficient becomes K1+ΔK11 (step 106) and when ΔV is between X and Y, the coefficient becomes K1+K12 (step 108). When ΔV is smaller than Y, the coefficient becomes K1+K13. The number of revolutions N and the load L at that time are detected (step 112) and are stored in the corresponding maps at a step 114. Since the range in which ΔA/F becomes great is substantially determined for a given engine, control at the transient time can be made conveniently if K1 is stored in the map of N and L. Incidentally, this K1 is always updated at the steady time.

Figure 13A:
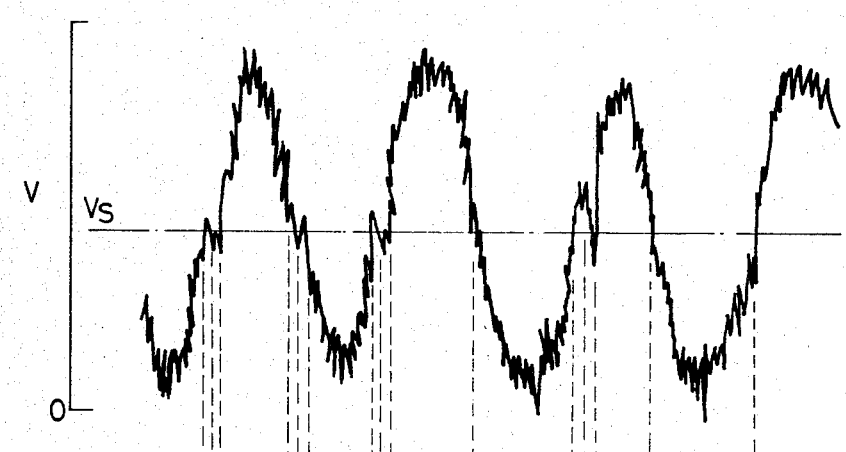
Figure 13B:
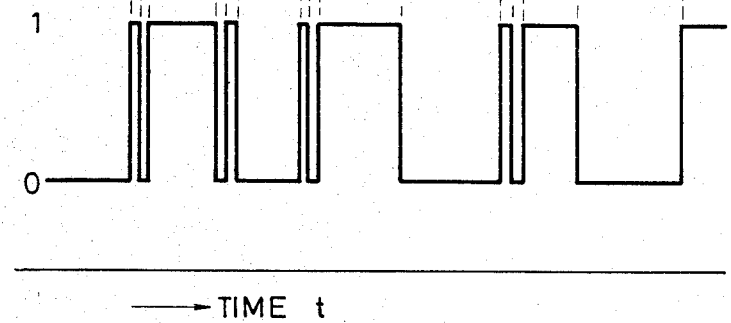

FIG. 13 shows another embodiment of the present invention which detects the degree of ΔA/F. When ΔA/F is great as shown in FIG. 13(a), the high frequency component adds to the waveform so that the waveform crosses the slice level $V_s$ more often than when ΔA/F is small and no high frequency component exists. In the proportional integration control circuit, $V_s$ and the electromotive force V of the sensor output V are compared by a comparator, so that the comparator output changes as shown in FIG. 13(b) and reverses between 0 and 1 by the number of times proportional to the magnitude of ΔA/F. In other words, if the number of times of this reversion is counted, the magnitude of ΔA/F can be determined and the integration constant may be changed.

Figure 2A:
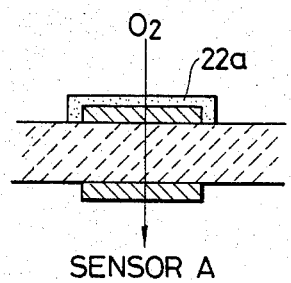
Figure 2B:
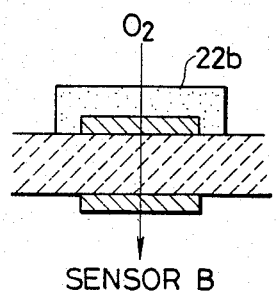
Figure 3:
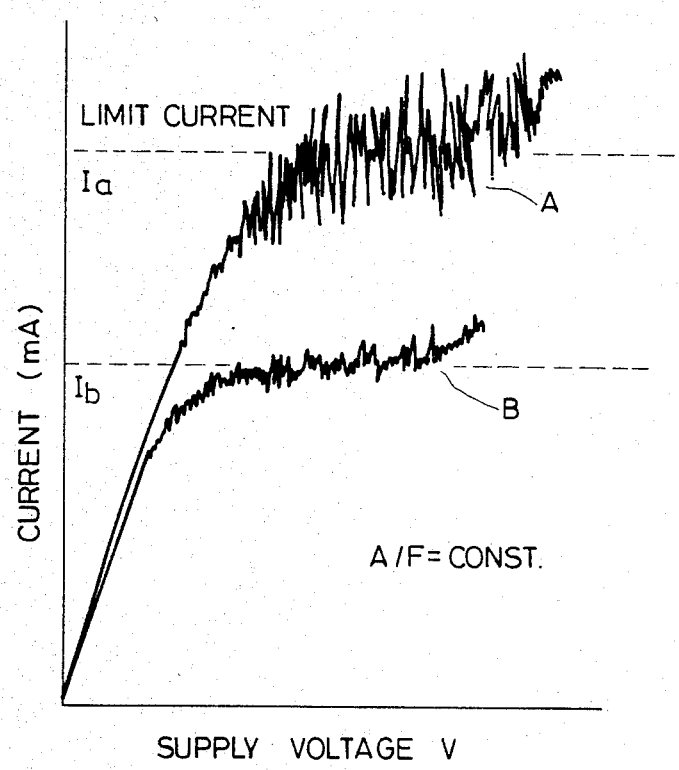
Figure 4:
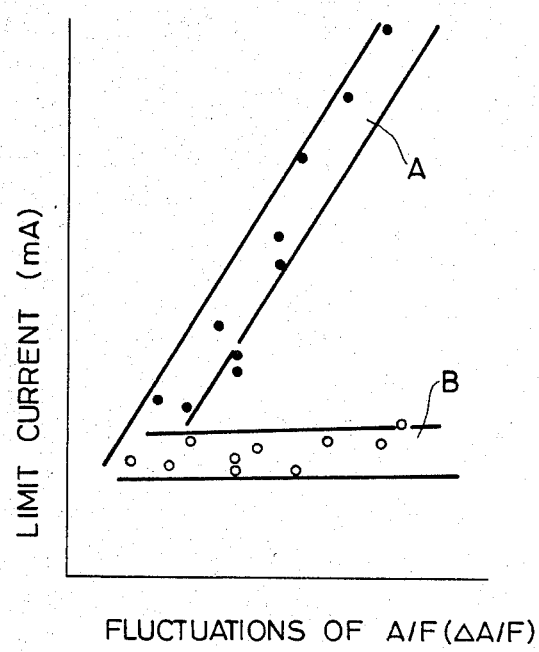
Figure 5:
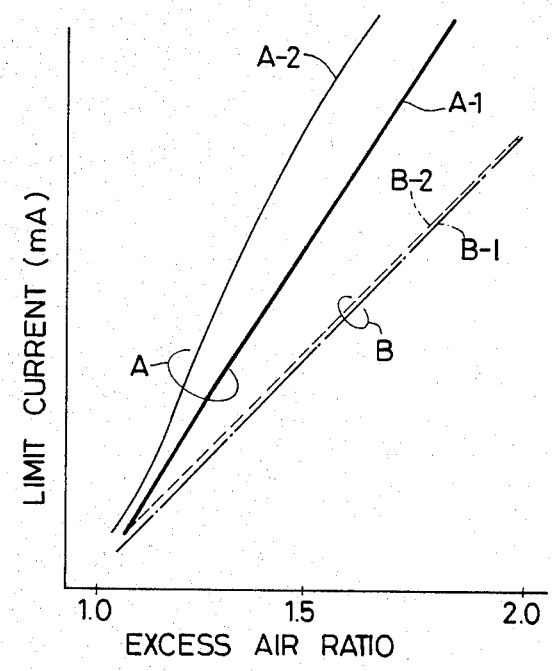
Figure 14:
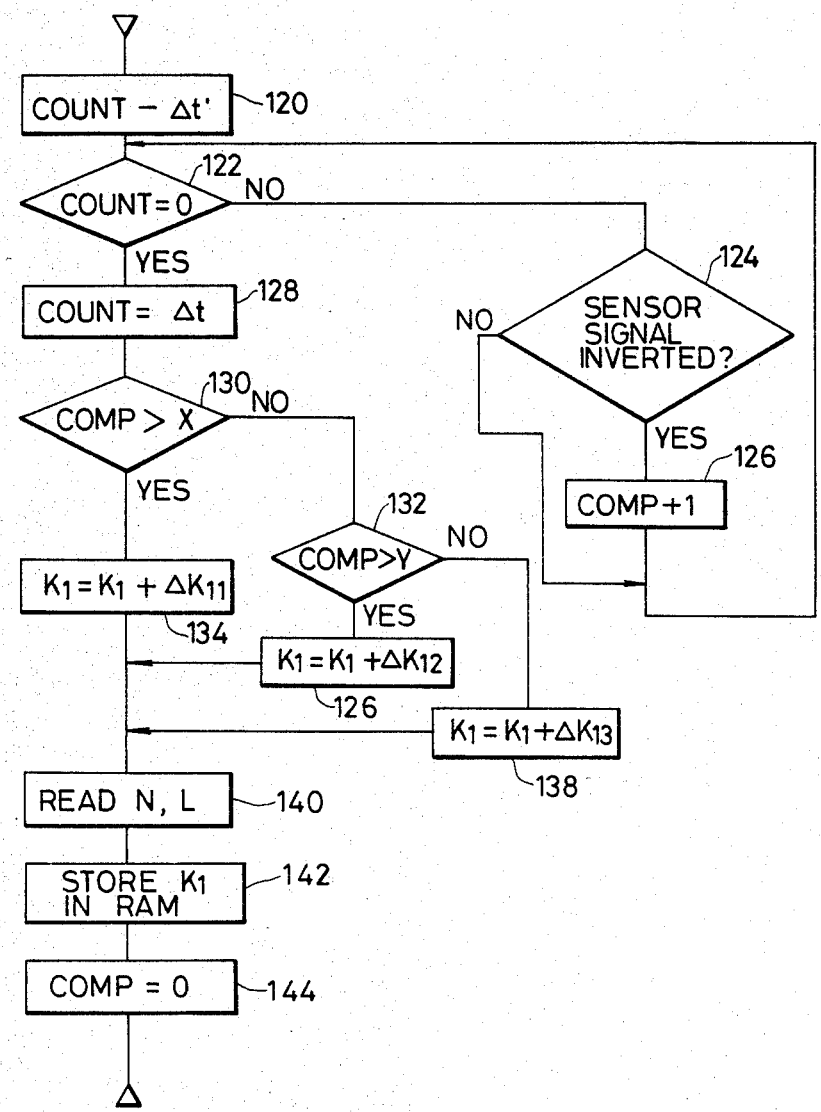

FIG. 14 shows the flowchart when this control is effected by a digital system. The overall construction is the same as that shown in FIGS. 2(a) and 2(b). Here, the read time of the number of reversals is designated "count". First, (count−Δt') is calculated at a step 120 with Δt' representing the time passed. At a step 122, the content of "count" is examined and if it is not found zero, that is, if the time is within the read period, whether or not the sensor signal has reversed is detected at a step 124. If reversal is detected, 1 is added to the number of reversals "comp" at a step 126. If the read-in time has ended at a step 122, Δt is set to "count" at a step 128.

The number of times of "comp", that is, the result of judgements 130 and 132, is used to modify the coefficient K1 of equation (2), which corresponds to the integration constants α, β, by ΔK11, ΔK12 and ΔK13 for the three different "comp" conditions: "comp">X, X>"comp">Y, and Y>"comp" (steps 134, 136 and 138). K1 is then stored in the map of the values N and L (steps 140 and 142), "comp" is cleared to zero (step 144), and a shift is made to the subsequent read-in period.

Figure 15A:
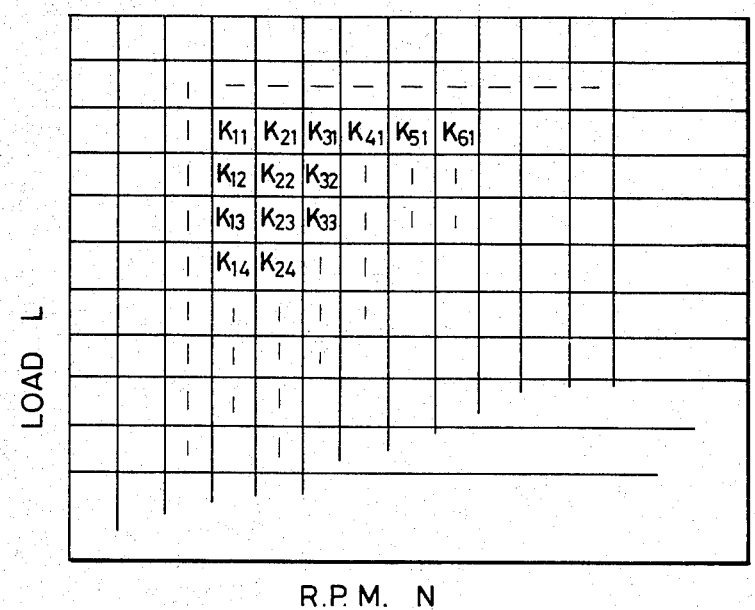
Figure 15B:
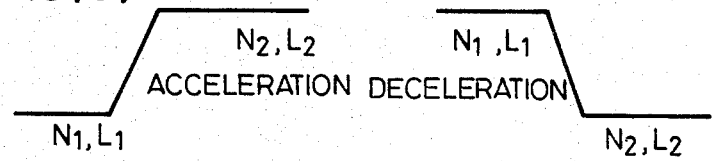
Figure 15C:
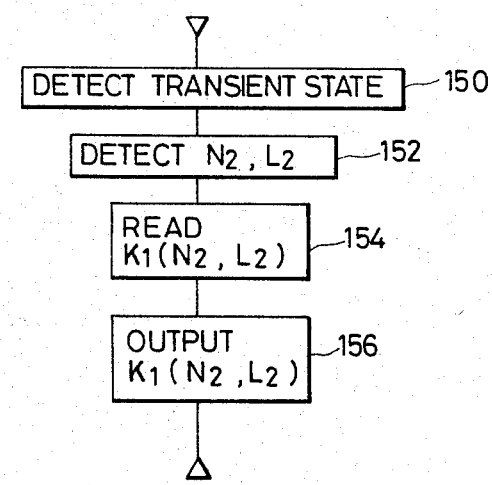

FIG. 15 shows an example of the map of the coefficient K1 and the transient control which has been described in the examples of FIGS. 12 and 14. Values of the coefficient K1 are stored in the N-L map of FIG. 15(a). In the steady state, the correction coefficient K1 is always updated. In FIG. 15(b), the running states before acceleration and deceleration are designated by $N_1$ and $L_1$, and the acceleration and deceleration are designated by $N_2$ and $L_2$. When a transient state occurs (step 150), as shown in FIG. 15(c), the values of $N_2$ and $L_2$ are detected (step 152), and the value of K1 corresponding to $N_2$ and $L_2$, which has ben updated and stored in the steady state, is read out (step 154) and is produced as the correction coefficient (step 156) which is used for the control. Even if the values $N_2$ and $L_2$ are within the range of large change of ΔA/F, the value K1 is produced faster than when it can be computed after the transient state, without any fear of the delay in the fuel control.

The system thus far described for correcting the correction coefficient can also be applied to the sensor according to the embodiment of FIG. 9.

Figure 16:
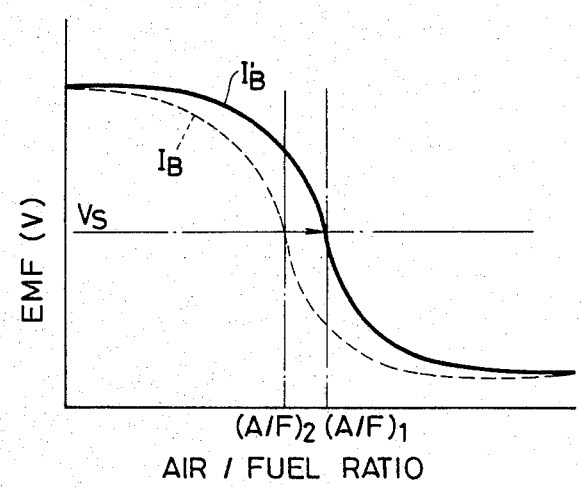
FIGS. 16 through 17a&b and 19a&b schematically illustrate still another embodiment of the present invention.

FIG. 16 shows another embodiment of the present invention, that is, a method in which the set current supplied to the sensor is changed in accordance with the change value ΔV. As has been described with reference to FIG. 7, the air fuel ratio changes if it is controlled by the constant current $I_0$ when there are large fluctuations in ΔA/F. Therefore, when the value of ΔA/F is so large that the limit current increases, the same air fuel ratio $\lambda_0$ can be controlled if the current $I_1$ ($I_1>I_0$) is supplied. By making use of this, as shown in FIG. 16, when the value of ΔA/F i.e., ΔV, is large, ΔV is detected to change the set current value $I_B$ supplied to the sensor to a value of $I_B'$ ($I_B'>I_B$) in accordance with the detected value of ΔV to make the air fuel ratio, which might otherwise be shifted to (A/F)$_2$, lean to (A/F)$_1$. The controlled A/F ratio can be prevented from becoming too rich when ΔA/F is large.

For this purpose, the control unit 90 in FIGS. 12(a) and 12(b) produces a set signal for the set current $I_B$. This set signal changes the feed current of the power source 23' as the variable current source and makes it coincide with $I_B$. The detail will be explained with reference to FIG. 17 showing its flow chart.

Figure 17A:
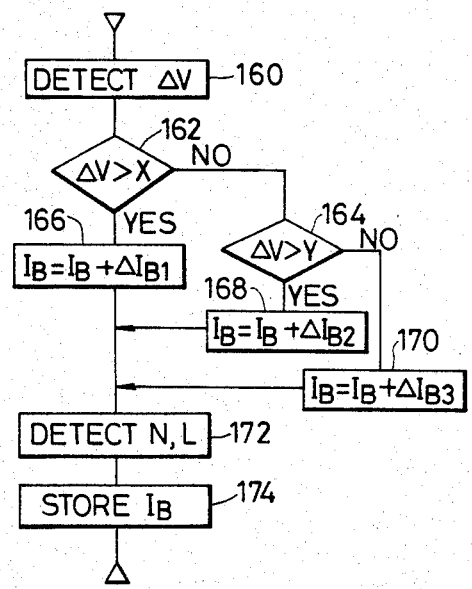
Figure 17B:
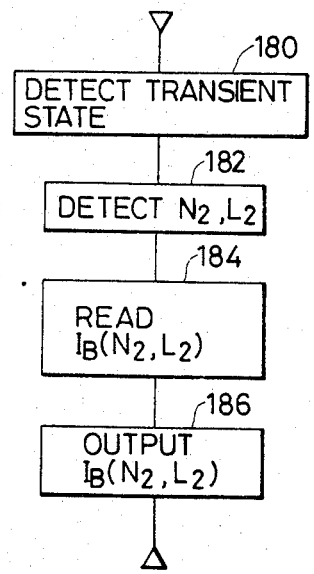
Figure 18:
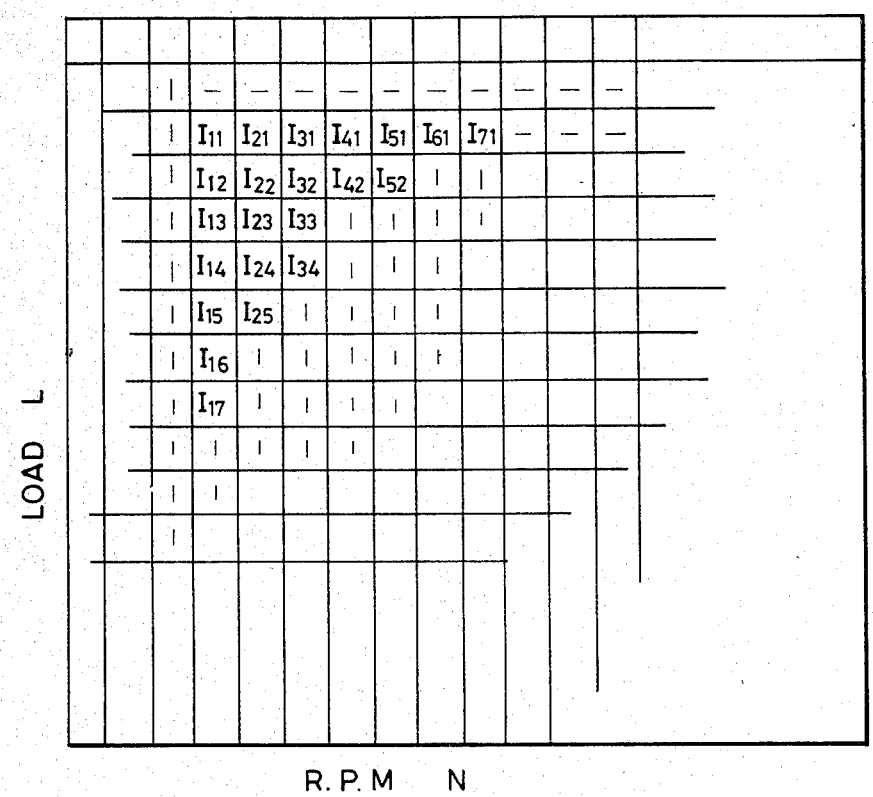

In FIG. 17(a), ΔV is detected at a step 160, the conditions, ΔV>X, X>ΔV>Y, and Y>ΔV are judged at steps 162 and 164, and $I_B$ is corrected by $\Delta I_{B1}$, $\Delta I_{B2}$ or $\Delta I_{B3}$ in an appropriate manner at step 166, 168 or 170. The corrected value is stored (steps 172 and 174) in the map (shown in FIG. 18) of the set current $I_B$ for N-L. When a transient state is detected (step 180), as shown in FIG. 17(b), the values of $N_2$ and $L_2$ are detected (step 182), and $I_B$ corresponding to $N_2$ and $L_2$ is promptly read out from the map (step 184) and is output (step 186) so that it can be used for the control.

Figure 19A:
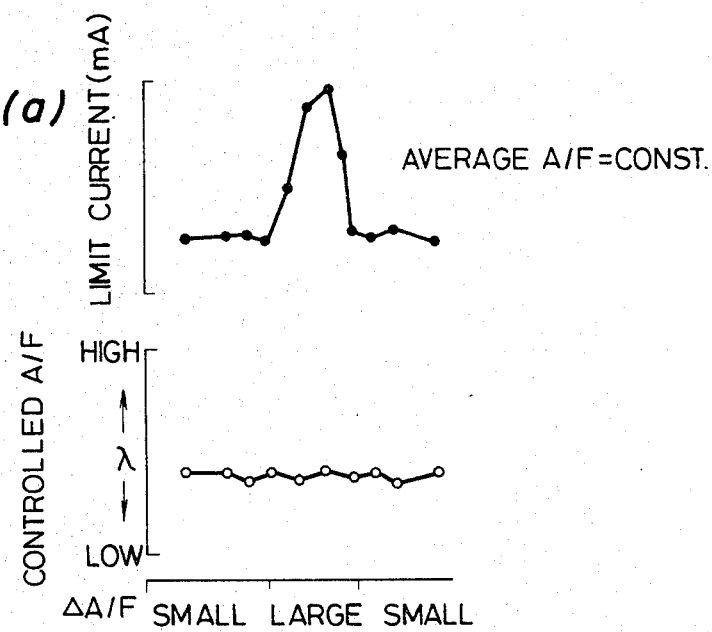
Figure 19B:
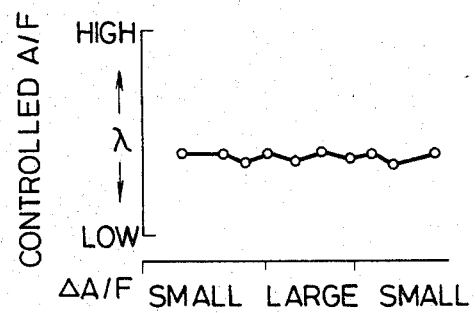

FIG. 19 shows the results obtained when the limit current becomes high when the value of ΔA/F is large, as shown in FIG. 19(a), and the set current corresponding thereto is supplied for the control (FIG. 19(b)). The controlled air fuel ratio is constant if the set current is changed in that way.

Figure 20:
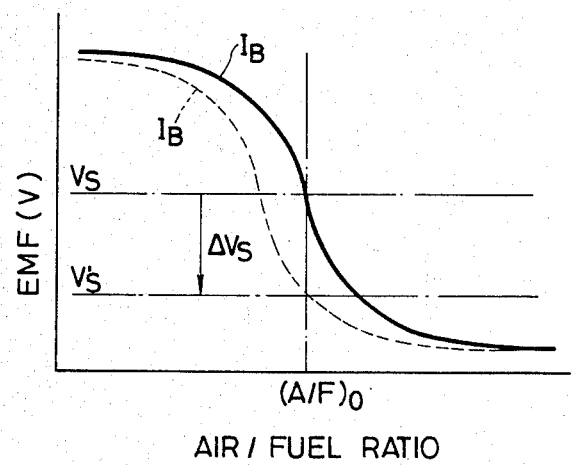
FIGS. 20, 21a&b and 22 schematically illustrate still another embodiment of the present invention.

FIG. 20 shows yet another embodiment of the present invention, in which not the set current $I_B$ but the slice level Vs' (Vs'=Vs−ΔVs) held by the control unit 90 is changed when ΔA/F is large. Then, even if ΔA/F is so large that the electromotive characteristics change, as shown by the broken line, the controlled A/F ratio does not change at the point (A/F)$_0$ if the control is done by using Vs'.

Figure 21A:
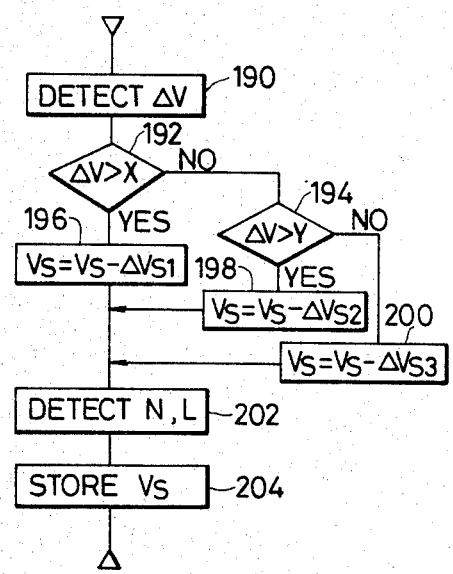
Figure 21B:
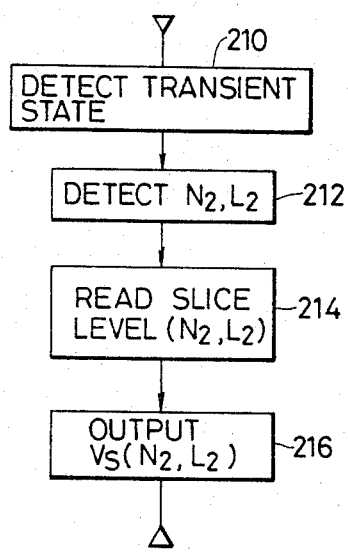
Figure 22:
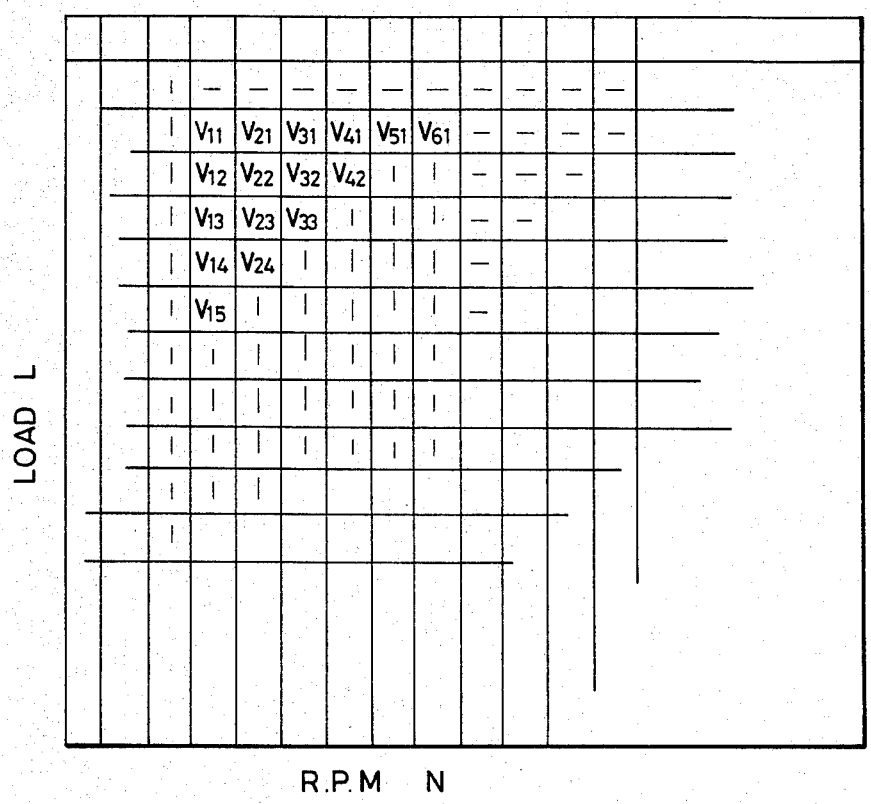

The flow chart for this is shown in FIG. 21. In FIG. 21(a), the value of ΔV is detected at a step 190, the conditions ΔV>X, X>ΔV>Y, and Y>ΔV are judged at steps 192 and 194, and Vs is accordingly corrected by $\Delta V_{S1}$, $\Delta V_{S2}$ or $\Delta V_{S3}$ at steps 196, 198 or 200. The value of Vs is then stored (steps 202 and 204) in the map (shown in FIG. 22) of the set current $I_B$ for N-L. When a transient state is detected (step 210), as shown in FIG. 21(b), $N_2$ and $L_2$ are detected (step 212), and the value of Vs corresponding to these values of $N_2$ and $L_2$ is promptly read out of the map (step 214) and is output (step 216) so that it can be used for the control.

Figure 23:
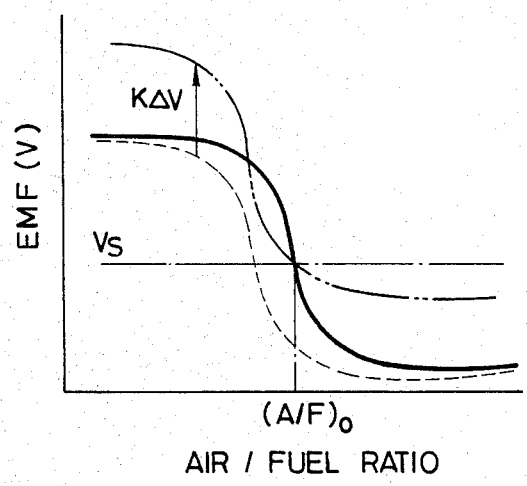
FIGS. 23 and 24 schematically illustrate still another embodiment of the present invention.
Figure 24:
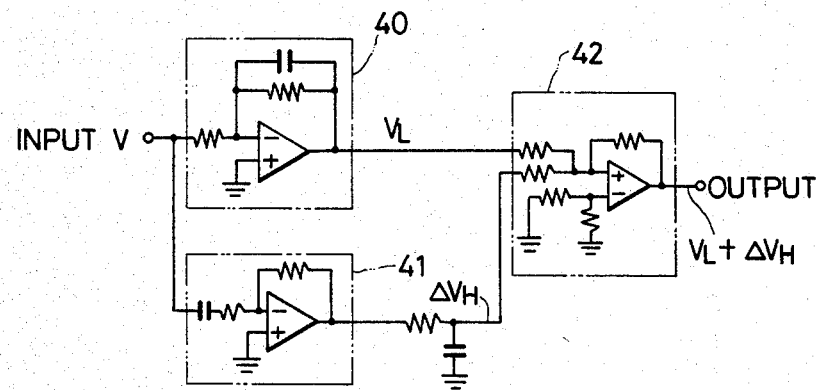

FIG. 23 shows still another embodiment of the present invention in which, when the characteristic of the electromotive force change from that of the solid line to that of the broken line as a result of the increase of ΔA/F, the value of ΔV corresponding to ΔA/F is detected and a compensation coefficient KΔV corresponding to this ΔV is added to the electromotive force to provide the signal shown by the double dot-dash line. If the control is conducted by that signal while the slice level is left at Vs, the same effect as that obtainable when the slice level is lowered is obtained so that the controlled A/F ratio does not change but stays at (A/F)$_0$. The circuit construction for this is shown in FIG. 24. A low frequency component $V_L$ is extracted from the output of the sensor portion 20' by a low-pass circuit 40, and the fluctuating high frequency component $\Delta V_H$ is provided by a high-pass circuit 41. The summation ($V_L+\Delta V_H$) is computed by an arithmetic circuit 42 and is applied to the control unit 90 and is used for the control.

Figure 25:
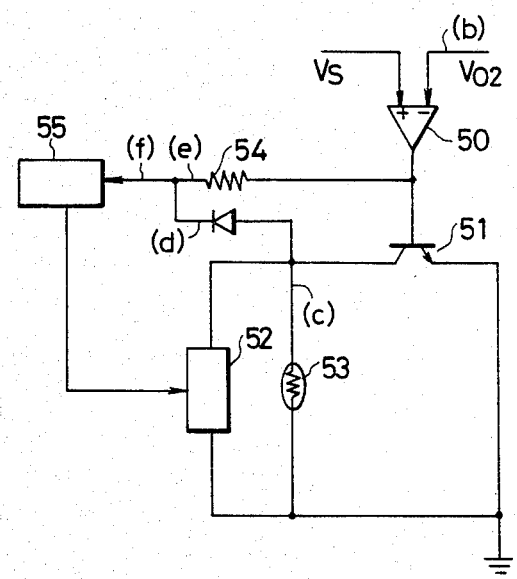
FIGS. 25 and 26a–f schematically illustrate still another embodiment of the present invention.
Figure 26A:
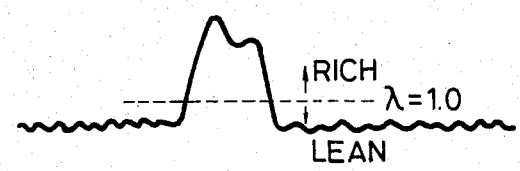
Figure 26B:
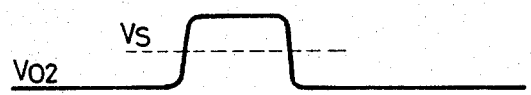
Figure 26C:
Figure 26D:
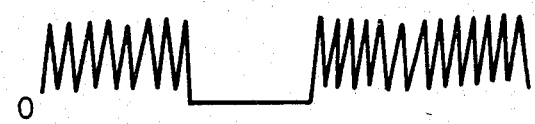
Figure 26E:
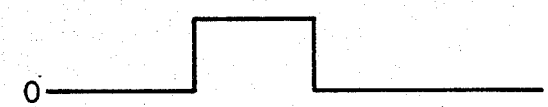
Figure 26F:

FIG. 25 shows a circuit by which the voltage (or current) supplied to the sensor is reduced to zero when the air fuel ratio enters the rich region of λ<1.0 when an air fuel ratio sensor of the oxygen pump type is used. If the voltage is applied to the solid electrolyte when the exhaust gas contains remarkably little oxygen, as in the rich region, the phenomenon arises that the oxygen ions migrate from the solid electrolyte. As a result, even if the air fuel ratio enters again the lean region, it takes some time for the oxygen ions to fill the solid electrolyte, and the sensor is insensitive during that period so that the responsive is delayed. The circuit of the embodiment of FIG. 25 is designed so that when the air fuel ratio enters the rich region, this is detected by the sensor whose electromotive force changes at $\lambda = 1.0$, and the voltage applied to the solid electrolyte is reduced to zero so that the oxygen ions are not attracted.

The signal $V_{02}$ of the sensors 20a and 20b for detecting $\lambda = 1.0$ and the slice level Vs are compared by a comparator 50. When the signal $V_{02}$ is ON $\lambda < 1.0$), a transistor 51 is turned on to prevent the flow of current from a power supply 52 to an air fuel ratio sensor 53. When the signal $V_{02}$ is OFF ($\lambda > 1.0$), on the other hand, the transistor 51 is turned off to supply the current to the air fuel ratio sensor 53. However, when the signal $V_{02}$ is ON but the output from the air fuel ratio sensor 53 is off, a constant voltage is applied in the meantime to a microcomputer 55 from a resistor 54 so as to keep a lean signal generated.

FIG. 26 shows the operation of the circuit of FIG. 25. FIG. 26(a) shows the changes in the CO component of the exhaust gases. When the CO concentration increases so that it enters the rich region, the output $V_{02}$ from the sensor for detecting $\lambda = 1.0$, shown in FIG. 26(b), exceeds the slice level Vs. The current I supplied to the air fuel ratio sensor 53 at this time by the actions of the comparator 50 and the transistor 51 drops to zero, as shown in FIG. 26(c). In other words, the output from the sensor 53 is off only within that rich region, as shown in FIG. 26(d). The off signal would be an enriching signal during the air fuel ratio control if left as it is, so that the control cannot be conducted because a control toward the lean state could not be provided. Therefore, an ON signal is generated during this time period, as shown in FIG. 26(e). This leaning signal must be input to the microcomputer 55. In other words, the signal input to the microcomputer 55 is the sum of the signals of FIG. 26(d) and (e), shown in FIG. 26(f). When the air fuel ratio enters the rich region, the current supplied to the sensor 53 is cut by this method, and the air fuel ratio is so controlled that it is promptly returned toward the lean state by the leading signal which is being generated in the meantime, thereby eliminating the insensitivity and the delay in response when in the rich region.

According to the present invention, the air fuel ratio detector can have a rapid response and can be used for an accurate air fuel ratio control.

What is claimed is:

1. An air/fuel ratio detector comprising:
a sensor using a current source for generating an output signal corresponding to an air/fuel ratio;
means for detecting a changing current component within the output signal from said sensor on the basis of the change of the air/fuel ratio with respect to time; and
means for compensating said output signal from said sensor by causing a correction of said output signal by subtracting a high frequency signal component within the detected current in said sensor output from a low frequency of said detected current component.

2. An air/fuel ratio detector comprising:
a sensor using a current source for generating an output signal corresponding to an air/fuel ratio, said sensor having a solid electrolyte and electrodes positioned on both sides of said electrolyte for detecting the electromotive force generated when a current flow across said electrodes;
means for detecting a changing component within the output signal from said sensor on the basis of the change of the air/fuel ratio with respect to time; and
means for compensating said output signal from said sensor by affecting a correction of said output signal by correcting a constant value of a proportional integration control in a closed circuit for said air/fuel ratio control on the basis of a high frequency signal component in said sensor output superimposed on a low frequency component.

3. An air/fuel ratio detector in accordance with claim 2 wherein said correcting a constant value of a proportional integration control in a closed circuit for said air/fuel ratio control is on the basis of the number of times the electromotive force of said sensor crosses a predetermined slice level within a predetermined period of time.

4. An air/fuel ratio detector comprising:
a sensor using a current source for generating an output signal corresponding to an air/fuel ratio, said sensor having a solid electrolyte and electrodes positioned on both sides of said electrolyte for detecting the electromotive force generated when a current flows across said electrodes;
means for detecting a changing component within the output signal from said sensor on the basis of the change of the air/fuel ratio with respect to time; and
means for compensating said output signal from said sensor by affecting a correction of said output signal by correcting a set current value supplied to said sensor on a basis of a high frequency signal component of said electromotive force of said sensor so as to make said air/fuel ratio lean.

5. An air/fuel ratio detector comprising:
a sensor using a current source for generating an output signal corresponding to an air/fuel ratio, said sensor having a solid electrolyte and electrodes positioned on both sides of said electrolyte for detecting the electromotive force generated when a current flows across said electrodes;
means for detecting a changing component within the output signal from said sensor on the basis of the change of the air/fuel ratio with respect to time; and
means for compensating said output signal from said sensor by affecting a correcting of said output signal by correcting a slice level held in a control unit so as to control said air/fuel ratio on the basis of a high frequency signal component of said electromotive force of said sensor.

6. An air/fuel ratio detector comprising:
a sensor using a current source for generating an output signal corresponding to an air/fuel ratio, said sensor having a solid electrolyte and electrodes positioned on both sides of said electrolyte for detecting the electromotive force generated when a current flows across said electrodes;
means for detecting a changing component within the output signal from said sensor on the basis of the change of the air/fuel ratio with respect to time; and
means for compensating said output signal from said sensor by affecting a correction of said output signal by correcting the electromotive force value in said sensor on the basis of a high frequency component of said electromotive force of said sensor.

* * * * *